United States Patent [19]

Riordan

[11] Patent Number: 5,866,142
[45] Date of Patent: Feb. 2, 1999

[54] SKIN TREATMENT SYSTEM

[76] Inventor: Neil H. Riordan, 7715 E. 32nd St. N., Wichita, Kans. 67226

[21] Appl. No.: 586,029

[22] Filed: Jan. 13, 1996

Related U.S. Application Data

[60] Provisional application No. 60/001,263, Jul. 20, 1995.

[51] Int. Cl.⁶ ..................................................... A61K 7/00
[52] U.S. Cl. .................................. 424/401; 424/DIG. 6; 514/836; 514/938
[58] Field of Search .............................. 424/401, DIG. 6; 514/938, 836; 548/339.1; 562/104

[56] References Cited

U.S. PATENT DOCUMENTS

| | | | |
|---|---|---|---|
| 4,201,235 | 5/1980 | Ciavatta | 132/7 |
| 4,503,041 | 3/1985 | Kashiwayama | 424/115 |
| 4,923,851 | 5/1990 | Carniglia | 514/23 |
| 4,946,870 | 8/1990 | Partain, III et al. | 514/777 |
| 5,135,913 | 8/1992 | Pickart | 514/16 |
| 5,141,964 | 8/1992 | Noel | 514/777 |
| 5,254,331 | 10/1993 | Mausner | 424/59 |
| 5,348,943 | 9/1994 | Pickart | 514/18 |
| 5,378,461 | 1/1995 | Neigut | 424/94.1 |
| 5,425,954 | 6/1995 | Thompson et al. | 424/401 |
| 5,567,427 | 10/1996 | Papadakis | 424/401 |
| 5,571,503 | 11/1996 | Mausner | 424/59 |
| 5,580,549 | 12/1996 | Fukuda et al. | 424/62 |
| 5,618,544 | 4/1997 | Brown | 424/401 |

*Primary Examiner*—S. Mark Clardy
*Assistant Examiner*—Robert H. Harrison
*Attorney, Agent, or Firm*—Philip J. Lee

[57] ABSTRACT

A skin treatment system comprises preparations for the topical application to the skin of histidine acting as a divalent cation chelator and exfoliant, pyridoxine and pantothenic acid and N-acetyl-D-glucosamine for increasing production of hyaluronic acid, superoxide dismutase and cysteine and vitamin E for decreasing the oxidative degradation of the hyaluronic acid, and pyroll carboxylic acid, or chemical salts thereof, and hyaluronic acid, or chemical salts thereof for providing increased hydration of the skin.

49 Claims, 1 Drawing Sheet

SKIN TREATMENT SYSTEM

RELATED APPLICATIONS

Benefit under Title 35, United States Code, Section 119(e) is claimed for the following U.S. Provisional Application which describes the invention which is the subject of this application:

Provisional Application Number: 60/001,263
Filed: Jul. 20, 1995
Titled: Skin Treatment System

BACKGROUND OF THE INVENTION

A. Field of Invention

This invention relates to the preparations for topical application to human skin and, more particularly, to new and improved skin cream or lotion compositions, which are especially useful in affecting the aging process of human skin.

B. Description of Related Art

The aging process of skin has been characterized by two main factors, the loss of elasticity and the loss of moisture, both of which are continuously lost over the course of the average human lifetime. Commercially available topical preparations have been designed to increase the moisture content of the skin. Most of the available topical moisturizing products provide only a short-term replenishment of moisture-providing ingredients. Some of such products contain glycolic acid alone and with other acids such as citric acid. Collectively, these acids may be referred to as "fruit acids," or "alpha-hydroxy" acids. The fruit acids are known to be capable, when applied to the skin, of aiding in the removal of older, dead, or keratinized skin cells, a process referred to as exfoliation. Exfoliation results in the exposure of the softer, younger skin cells, which otherwise lay below the older cells, and in this manner, exfoliation results in softer, younger appearing skin. Another positive consequence of the removal of the dead skin cells is that the still living, younger skin cells which are now exposed, produce, as a protective mechanism, increased amounts of at least one type of glycosaminoglycan molecule. Glycosaminoglycan molecules produced by the skin include hyaluronic acid, chondroitin sulfate, and dermatan sulfate. Hyaluronic acid is known to be produced in higher quantities by the skin cells in response to exfoliation. Hyaluronic acid has a large capacity for hydration. One gram of hyaluronic acid is able to hydrate to a volume of 3 liters. The exposed, younger skin cells produce more hyaluronic acid than the older cells provided there are present sufficient substrates and co-factors required for hyaluronic acid synthesis by the skin cells. As a result, after exfoliation with fruit acids, a higher concentration of hyaluronic acid is produced in the skin. The hyaluronic acid, being a hydrating molecule, and being located deeper in the skin than topically applied hyaluronic acid or other topically applied moisturizers results in the ability of fruit acid application to the skin to act as, in effect, a long term moisturizer. The length of time of increased hydration of the skin can vary depending on the concentration and number of applications of fruit acids, as well as the endogenous stores of substrates and co-factors that are required and available to the skin for hyaluronic acid production. The combination of the two effects of topically applied fruit acids, exfoliation and increased skin production of hyaluronic acid, is believed to result in a lessening of the appearance of skin wrinkles.

A negative consequence of the reliance upon exfoliation to appreciatively increase the amount of hyaluronic acid in the skin is that the skin, having been stripped of its protective layer of keratinized cells, is relatively unprotected but nevertheless is exposed to the elements. The younger, unprotected skin is susceptible to damage by environmental factors such as chemicals, and sunlight. It is also noted that after long-term use of fruit acids for exfoliation, endogenous stores of substrates and co-factors required for the production of hyaluronic acid can become depleted. As a result, the hyaluronic acid content, and subsequently the moisture content of the skin can actually be reduced by long-term, or chronic topical use of fruit acids in concentrations capable of exfoliation. Another disadvantage of the use of fruit acids is the fact that their use has been associated with a significant amount of irritation.

Many skin cream compositions which are commercially available also address the other major component of skin aging, the loss of elasticity, through the use of moisturizers. One of the mechanisms of the loss of elasticity in aging skin is through the loss of elastin, a human protein which is a major component in elastic fibers and provides the skin with much of its elastic qualities. The break down of elastin is characterized by the deposition of lipids in the protein fold, followed by the attraction, by the lipids, of mineral salts. The accumulation of mineral salts, in particular calcium, decreases the elasticity of the elastin, and when the elastin molecule loses enough of its elasticity and becomes rigid, the molecule will break rather than elongate if enough tension is applied. When the elastin molecules break down, they are removed by endogenous immune surveillance mechanisms and may not be replaced at the same rate, resulting in a net loss of elastin in the skin tissue. At the area at the lateral folds of the eyes, the forehead, and on the neck, the chronic net loss of elastin, allows for the formation of wrinkles. Some commercial products include the molecule elastin in their formulations, However, as is the case with skin care moisturizers, there is no evidence that this exogenous elastin penetrates to a level that would be helpful, or that it remains in the skin long enough to provide any level of protection from, or reversal of, wrinkles. The known, available skin care products have not been demonstrated to interfere with the break down of elastin and the age-associated decrease in skin elasticity which in part characterizes the aging process of skin.

SUMMARY OF THE INVENTION

The present invention comprises formulations for skin cream or lotion compositions which are topically applied to the skin and contain chemical agents which in combination have the following properties:

1. being a divalent cation chelator;
2. being capable of the exfoliation of dead and keratinized skin cells without irritating the skin;
3. being capable of increasing production of hyaluronic acid;
4. providing rate limiting substrates for the production of hyaluronic acid by skin cells;
5. being capable of reducing the oxidative degradation of hyaluronic acid;
6. being capable of short term hydration of the skin; and
7. being a water or lipid based delivery vehicle.

The present invention comprises preferably the use of the amino acid, histidine, or a chemical derivative of histidine as the divalent cation chelating agent. When applied topically, and in adequate concentrations to the skin, histidine is an effective agent for simultaneously achieving exfoliation of dead and keratinized skin cells without irritating the skin as well as for chelating the calcium ions from the elastin molecules in the skin.

The present invention further comprises concentrations of pyridoxine and pantothenic acid that are effective for inducing increased production of the hydrating glycosaminoglycan, hyaluronic acid, including in skin cells that have not been treated extensively, or at all, with an exfoliating agent. Inducing increased production of hyaluronic acid independently of exfoliation causes the hydration of the skin without increasing the risk of environmental damage to young skin cells.

Hyaluronic acid, which is produced by all living skin of human beings, is a hydrating molecule, one gram being known to hydrate to a volume of 3 liters. When young skin cells are exposed after exfoliation, they produce larger quantities of hyaluronic acid which is a glycosaminoglycan which is composed of a chain of alternating, repeating, D-glucuronic acid and N-acetyl-D-glucosamine molecules. N-acetyl-D-glucosamine is known to be a rate-limiting factor in the hyaluronic acid production by living cells.

The topical application of glucosamine, or a readily metabolizable form of the glucosamine molecule, in particular N-acetyl-D-glucosamine, assists in the continued production of hyaluronic acid by increasing the available supply of a rate limiting substrate in the production of hyaluronic acid by skin cells. The molecules superoxide dismutase, cysteine, and vitamin E, are added to the preferred embodiment of the present invention to stop the oxidative degradation of the hyaluronic acid present in the skin, thereby slowing the depletion of that hydrating substance. The present invention includes the direct topical application of short term hydrating molecules such as pyroll carboxylic acid, or chemical salts thereof, and hyaluronic acid, or chemical salts thereof to the skin to provide hydration results that are more immediate than the results of the induction of increased production of hydrating substances by the skin.

A principal objective of the present invention is to provide a new and improved skin care system for topical application which meets the foregoing requirements and which is capable of, and is safe to use for, the exfoliation of the skin without irritation.

Another and further object and aim of the present invention is to provide a new and improved skin care system for topical application which meets the foregoing requirements and which is capable of, and is safe to use for, providing to the hyaluronic acid-producing skin cells, substances which are required by the skin for the production of hyaluronic acid.

Yet another and further object and aim of the present invention is to provide a new and improved skin care system for topical application which meets the foregoing requirements and which is capable of inducing skin cells to produce hyaluronic acid, with a minimum of exfoliation.

Yet another and further object and aim of the present invention is to provide a new and improved skin care system for topical application which meets the foregoing requirements and which is capable of providing increased moisturization of the skin afforded by fruit acid exfoliation with a minimum of exposure of young skin cells to damaging environmental factors.

Yet another and further object and aim of the present invention is to provide a new and improved skin care system for topical application which meets the foregoing requirements and which is capable of providing to the hyaluronic acid-producing skin cells, substances required for the production of hyaluronic acid.

Yet another and further object and aim of the present invention is to provide a new and improved skin care system for topical application which meets the foregoing requirements and which is capable of the inhibition or reversal of the break down of the molecule elastin in the skin.

Yet another and further object and aim of the present invention is to provide a new and improved skin care system for topical application which meets the foregoing requirements and which is capable of the inhibition of the oxidative degradation of hyaluronic acid in the skin.

Other objects and advantages of the invention will become apparent from the Description of the Preferred Embodiments and will be in part pointed out in more detail hereinafter.

Further features of the present invention are set forth in the following detailed description.

The invention consists in the elements, combination of elements and use thereof as hereinafter described and the scope of the invention will be indicated in the appended claims.

DETAILED DESCRIPTION OF THE INVENTION

Figure 1:
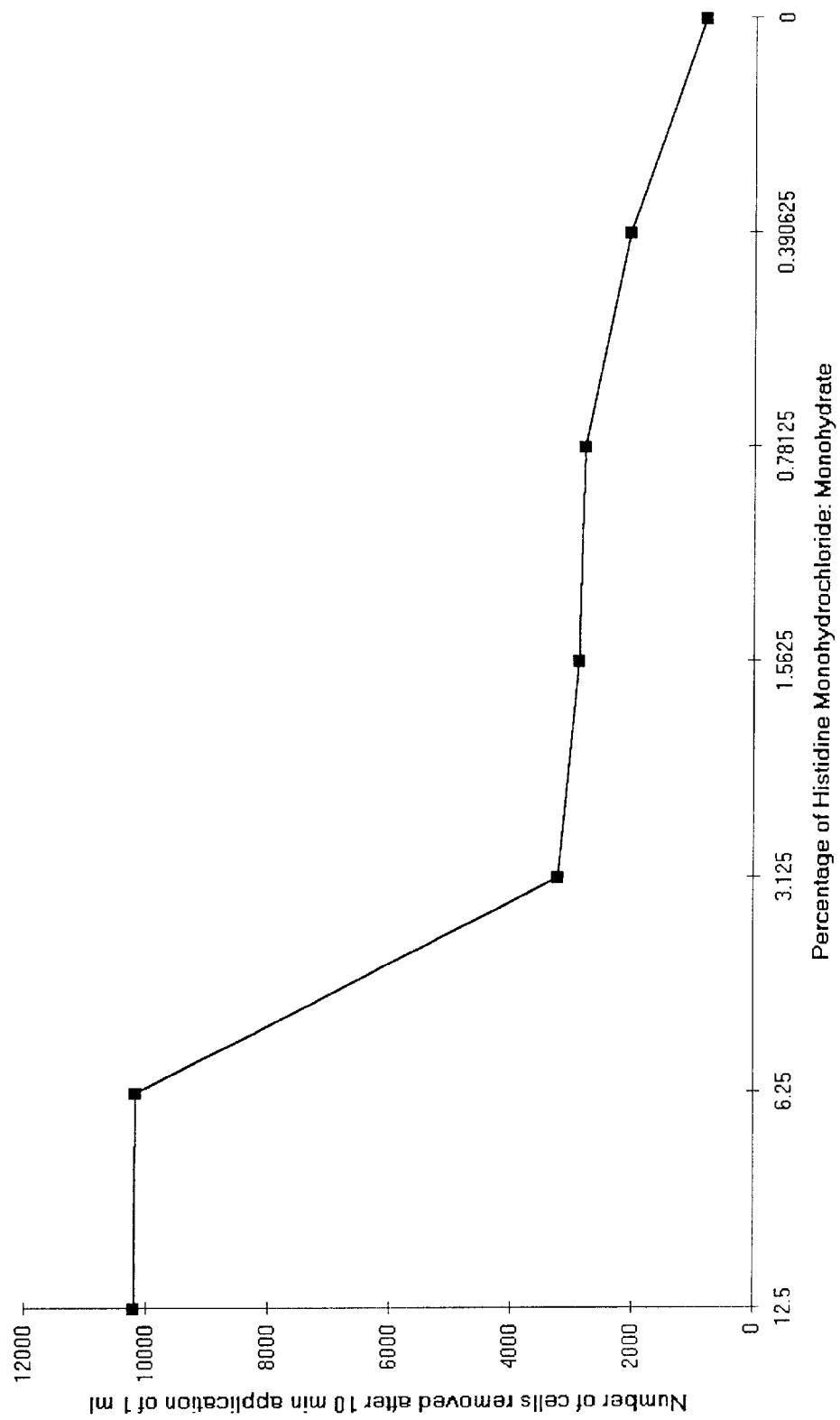

The present invention comprises a combination of chemical agents for topical application to the skin. The topical formulations described in the detailed description will be referred to as, for the sake of simplicity, creams; the preferred embodiment of the present skin care system consists of a first preparation with a water soluble base and a second preparation having an emulsified solvent base containing both water and lipids. There are few limitations to the types of solvents which can be utilized in the skin care system. The most preferable solvents being those in which the ingredients are soluble and are pleasing to the consumer.

The preferred embodiment of the water based preparation includes a divalent cation chelator for the purpose of reducing the concentration of mineral salts, particularly calcium salts. As described above, the aging human skin is characterized in part by a loss in elasticity which is attributed to the attraction of mineral salts, particularly calcium salts, by lipids deposited in the protein folds of elastin molecules, increasing the rigidity of, and solidifying the aging elastin molecules. The molecule histidine, and other divalent cation chelators, are able to remove when applied topically to the skin of human beings, mineral salts, in particular, the mineral salt calcium. It is believed that the topical application of cation chelator, in sufficient quantities, will create a concentration gradient of calcium, from deep to superficial, to occur, resulting in a reduction in the amount of calcium available to bind to elastin proteins, and, if the removal of calcium salts is aggressive enough, the concentration gradient created is significant enough that mineral salts already in the elastin protein folds are dislodged, thereby reversing a major step in the break down of elastin.

Taurine and histidine are both amino acids and divalent cation chelators that were found to have the ability to remove calcium from the skin of humans. More particularly, histidine was found to chelate significant amounts of calcium from human skin at concentrations that were non-irritating. Histidine was found to cause an immediate softening of the skin after it is washed off and the mechanism for this softening, appears to include exfoliation of older skin cells. A variety of preparations including Histidine in concentrations from 0.1 to 20% by weight were tested and found to exhibit exfoliant activity. The exfoliant activity of Histidine is believed to be caused by the breakage of calcium dependent bonds and cross bridges contained in the intercellular proteins of the skin rather than the direct caustic effect of conventional exfoliants.

FIG. 1 demonstrates the exfoliant activity of an inexpensive form of histidine, histidine monohydrochloride: monohydrate.

As illustrated in FIG. 1, in an experiment utilizing skin treated with various concentrations of histidine, it was found that, in a dose dependent manner, histidine was able to remove dead and keratinized skin cells. For the experiment, one milliliter of solutions containing either normal saline, or normal saline with 12.5, 6.25, 3.13, 1.56, 0.78, and 0.39 percent histidine monohydrochloride:monohydrate, respectively were placed onto the skin of volunteers. After 10 minutes of the experimental solutions being in contact with the skin, the skin at each site was scraped with a glass slide to collect skin cells. 9 samples at each concentration were collected. The epithelial cells from each sample were counted using a model ZM, Coulter particle counter. The Coulter counter was calibrated using a Neubauer hemacytometer. The counting of cells by the particle counter was confirmed by microscopy. The y-axis of FIG. 1 represents the total number of cells collected, while the x-axis represents the concentration of histidine used. At no concentration did any of the volunteers have demonstrable irritation or dermatitis or any other adverse side effect related to the application of the histidine.

The preferred embodiment of the water soluble preparation of the present invention, therefore, contains the molecule histidine, or any one of its salts in a solution, or suspension, in a concentration by weight from 0.1 to 20%. More preferably, the concentration of histidine is from 0.3 to 12.5% by weight, and most preferably in a concentration between 0.6 and 0.8% by weight.

Alternatively, the molecules taurine, Ethylenediaminetetraacetic acid ("EDTA"), or EGTA, or other divalent cation chelating agents could be substituted for histidine. A preparation of a concentrated solution of EDTA was experimentally applied to the skin, applying it to a forearm, while applying a control mixture to the other forearm. After 10 minutes, both solutions were rinsed from the forearms, and the arms dried and the result was that the treated arm was observably softer than the control arm. The subjective observation was confirmed by several other observers. A solution containing 1% by weight of EDTA was applied to the one forearm for several applications. Topical application of EDTA in higher concentrations was found to cause skin irritation. A 0.5% solution of EDTA has been found to have similar softening effects without irritation while a 1% solution by weight of EDTA caused skin irritation.

The hypothesis that the topical application of a cation chelator such as EDTA was capable of removing calcium from human skin was tested experimentally. 2 Milliliters of 0.5% EDTA solution were placed onto one side of the previously washed (with cation-free soap) foreheads of three volunteers. A control solution of 0.5% sodium chloride was placed on the other side of each volunteer's forehead. After 10 minutes, the remaining solution was collected by scraping the skin. An equal weight of this solution from treated and control scrapings was then pooled for each group respectively and rehydrated to a volume of 5 Ml. Each of the samples was then analyzed for calcium concentration in a trace elements laboratory using an ICP analyzer. The treated samples contained 16.58 parts per million (PPM) of calcium, while the control sample contained 4.877 PPM of calcium, thus demonstrating that a cation chelator was capable of removing a significant quantity of calcium from the skin of humans.

The preferred embodiment of the water based preparation, also contains a form of the molecule glucosamine, preferably N-acetyl-glucosamine. When added to the composition, N-acetyl-D-glucosamine ensures that the lack of a usable form of glucosamine does not rate-limit the hyaluronic acid production, that is induced either by the above-mentioned exfoliation or the alternative method described below. The preferred concentration of N-acetyl=D-glucosamine is between 0.005 and 12% by weight, more preferably 0.01 and 5% by weight, and most preferably 0.1% by weight. The best results from the use of the water soluble preparation are obtained when it is applied and allowed to remain on the skin for approximately 10 minutes, when it is gently removed by rinsing it off with cool water.

The preferred embodiment of the invention further comprises a second preparation having an emulsified water and lipid base that is most beneficially used by topical application and being left on the skin after application. Since the second preparation is to be left on the skin, it contains the molecule N-acetyl-D-glucosamine, which is useful for the same reasons stated above, but which will be available for a longer period of time to the skin cells.

The preferred embodiment of the second preparation also contains the molecules pantothenic acid and pyridoxine, two vitamins which appear to work synergistically to increase cellular production of hyaluronic acid. The inclusion of pantothenic acid and pyridoxine is an alternative method of inducing hyaluronic acid production without relying on the exfoliation of the skin as described above to increase cellular production of hyaluronic acid. Topically applied pantothenic acid and pyridoxine were experimentally shown to be capable of inducing the production of hyaluronic acid in human skin. Approximately 0.5 mL of a solution containing 0.08% pantothenic acid and 0.2% pyridoxine in an aqueous base was applied to the skin of one hand of an individual, and the opposite hand served as a control, having only water applied to it at the same time. Within one week, the skin on the active ingredient treated hand was observed to be noticeably softer than the control treated hand. Then the active and control solutions were applied nearly daily for six weeks. Two weeks after discontinuation of the use of both of the solutions, a small piece of skin was removed from each of the treated hands (superficial biopsy), to obtain 100 micrograms of tissue. The tissue was digested and tested for hyaluronic acid using a very sensitive radio-immuno-assay. The skin sample from the active ingredient treated hand contained a much higher concentration of hyaluronic acid (522.51 nanogram/mg) than the skin sample from the control treated hand 115.58 nanogram/mg). This represents a greater than 450% increase in the amount of hyaluronic acid in the treated skin versus the control. Because the sample was taken 2 weeks after discontinuation of product use, a long term effect on the hyaluronic acid content of the skin by the topical application of a combination of pantothenic acid and pyridoxine is suggested. The preferred embodiment of the second preparation of the invention contains pantothenic acid in a concentration from at least 0.001 to a maximum of 2% by weight, with a more effective range of concentration being from 0.1% to 1.5% by weight. The most preferable concentration of pantothenic acid was found to be 0.8%. The preferred embodiment of the second preparation of the invention also contains pyridoxine in a concentration from at least 0.0025% to a maximum of 5% by weight, with a more effective range of concentration being from 0.25% to 3.75% by weight. The most preferable concentration of pyridoxine was found to be 2%.

The preferred embodiment of the second preparation also contains the enzyme super oxide dismutase (SOD), and the molecules cysteine, and tocopherol (vitamin E) which are known to inhibit the oxidative degradation of the molecule hyaluronic acid. Each of these three molecules are added in a concentration ranging from 0.001% to 1.5% by weight, most preferably in a concentration of between 0.1 and 0.5% by weight. By protecting the hyaluronic acid molecule from degradation, these additional agents provide for longer lasting hyaluronic acid molecules and subsequently, longer lasting hydration of the skin.

In addition, the preferred embodiment of the second preparation includes the sodium salt of pyroll carboxylic acid (NaPCA) and the sodium salt of hyaluronic acid. Those molecules are included in the preferred embodiment of the present invention in the concentrations of 0.5% and 0.2% respectively to produce short-term hydration.

According to the foregoing, the preferred embodiment of the skin care system of the present invention includes the following:

A. The first, water soluble, preparation comprising the following active ingredients:
 1. histidine in a concentration by weight from 0.1 to 20%, and
 2. N-acetyl=D-glucosamine in a concentration by weight from 0.005 and 12% by weight; and B. The second, emulsified water and lipid based preparation comprising the following active ingredients:
 1. N-acetyl-D-glucosamine, and
 2. pantothenic acid in a concentration from at least 0.001 to a maximum of 2% by weight, and
 3. pyridoxine in a concentration from at least 0.0025% to a maximum of 5% by weight, and
 4. super oxide dismutase (SOD) in a concentration ranging from 0.001% to 1.5% by weight, and
 5. cysteine in a concentration ranging from 0.001% to 1.5% by weight, and
 6. tocopherol (vitamin E) in a concentration ranging from 0.001% to 1.5% by weight, and
 7. the sodium salt of pyroll carboxylic acid (NaPCA) in a concentration of 0.5% by weight, and
 8. the sodium salt of hyaluronic acid in a concentration of 0.2% by weight.

It will be appreciated that the foregoing may be altered in a number of ways with differing but still beneficial results. Specifically, the concentrations of active agents as given herein are believed to be optimal; however, it is anticipated that significant alterations in exact concentrations may be made without rendering the preparation harmful or ineffective. It will further be appreciated that the treatment of the present invention may be formulated entirely in a single water based preparation or in dual preparations as described without a water and lipid emulsion base for the second preparation. In the event only water based preparations are used, the hydrophobic tocopherol would preferably be emulsified, either chemically or physically for the better results. In addition, it is expected that the addition of other known skin treatment agents to the treatment preparation of the present invention may have beneficial results.

While the preferred constituents and method of the foregoing invention have been set forth for purposes of illustration, the foregoing description should not be deemed a limitation of the invention herein. Accordingly, various modifications, adaptations and alternatives may occur to one skilled in the art without departing from the spirit and the scope of the present invention.

What is claimed is:

1. A skin care treatment for topical application comprising a divalent cation chelator selected from the group consisting of histidine, taurine, and pharmaceutically acceptable derivatives or salts thereof in a concentration which is capable of exfoliating dead skin cells without being irritating to the skin, and pyridoxine and pantothenic acid in concentrations capable of inducing cellular production of hyaluronic acid, and a form of glucosamine.

2. The skin care treatment of claim 1, further comprising super oxide dismutase in a concentration from about 0.001 to about 4.5% by weight and tocopherol in a concentration from about 0.001 to about 1.5% by weight.

3. The skin care treatment of claim 2, further comprising cysteine in a concentration from about 0.001 to about 1.5% by weight.

4. The skin care treatment of claim 3, further comprising sodium pyroll carboxylate in a concentration of about 0.5% by weight.

5. The skin care treatment of claim 4, further comprising a sodium salt of hyaluronic acid in a concentration of about 0.2% by weight.

6. The skin care treatment of claim 5, wherein the divalent cation chelator is histidine monohydrochloride; monohydrate in a concentration from about 0.1 to 20% by weight.

7. The skin care treatment of claim 6, wherein the concentration of pyridoxine is from about 0.0025% to about 5% by weight, the concentration of pantothenic acid is from about 0.001% to about 2% by weight, and wherein the form of glucosamine is N-acetyl-D-glucosamine in a concentration from about 0.005% to about 12% by weight.

8. The skin care treatment of claim 7, further comprising a water soluble base.

9. The skin care treatment of claim 8, further comprising a water and lipid emulsion base.

10. A skin care treatment for topical application comprising pyridoxine and pantothenic acid in concentrations capable of inducing cellular production of hyaluronic acid, a form of glucosamine, super oxide dismutase in a concentration from about 0.001 to about 4.5% by weight, and tocopherol in a concentration from about 0.001 to about 1.5% by weight.

11. The skin care treatment of claim 10, further comprising cysteine in a concentration from about 0.001 to about 1.5% by weight.

12. The skin care treatment of claim 11, further comprising sodium pyroll carboxylate in a concentration of about 0.5% by weight.

13. The skin care treatment of claim 12, further comprising a sodium salt of hyaluronic acid in a concentration of about 0.2% by weight.

14. The skin care treatment of claim 13, further comprising a divalent cation chelator in a concentration which is capable of exfoliating dead skin cells without being irritating to the skin.

15. The skin care treatment of claim 14, wherein the cation chelator is selected from the group consisting of histidine, taurine, and pharmaceutically acceptable derivatives or salts thereof.

16. The skin care treatment of claim 15, wherein the divalent cation chelator is histidine monohydrochloride; monohydrate in a concentration from about 0.1 to 20% by weight.

17. The skin care treatment of claim 16, wherein the concentration of pyridoxine is from about 0.0025% to about 5% by weight, the concentration of pantothenic acid is from about 0.001% to about 2% by weight, and wherein the form of glucosamine is N-acetyl-D-glucosamine in a concentration from about 0.005% to about 12% by weight.

18. The skin care treatment of claim 17, further comprising a water soluble base.

19. The skin care treatment of claim 18, further comprising a water and lipid emulsion base.

20. A skin care treatment for topical application comprising super oxide dismutase in a concentration from about 0.001 to about 4.5% by weight and tocopherol in a concentration from about 0.001 to about 1.5% by weight, and pyridoxine and pantothenic acid in concentrations capable of inducing cellular production of hyaluronic acid.

21. The skin care treatment of claim 20, further comprising a form of glucosamine.

22. The skin care treatment of claim 21, further comprising cysteine in a concentration from about 0.001 to about 1.5% by weight.

23. The skin care treatment of claim 22, further comprising sodium pyroll carboxylate in a concentration of about 0.5% by weight.

24. The skin care treatment of claim 23, further comprising a sodium salt of hyaluronic acid in a concentration of about 0.2% by weight.

25. The skin care treatment of claim 24, further comprising a divalent cation chelator in a concentration which is capable of exfoliating dead skin cells without being irritating to the skin.

26. The skin care treatment of claim 25, wherein the cation chelator is selected from the group consisting of histidine, taurine, and pharmaceutically acceptable derivatives or salts thereof.

27. The skin care treatment of claim 26, wherein the divalent cation chelator is histidine monohydrochloride; monohydrate in a concentration from about 0.1 to 20% by weight.

28. The skin care treatment of claim 27, wherein the concentration of pyridoxine is from about 0.0025% to about 5% by weight, the concentration of pantothenic acid is from about 0.001% to about 2% by weight, and wherein the form of glucosamine is N-acetyl-D-glucosamine in a concentration from about 0.005% to about 12% by weight.

29. The skin care treatment of claim 28, further comprising a water soluble base.

30. The skin care treatment of claim 29, further comprising a water and lipid emulsion base.

31. A skin care treatment for topical application comprising N-acetyl-D-glucosamine, pyridoxine and pantothenic acid in concentrations capable of inducing cellular production of hyaluronic acid, super oxide dismutase in a concentration from about 0.001 to about 4.5% by weight and tocopherol in a concentration from about 0.001 to about 1.5% by weight.

32. The skin care treatment of claim 31, further comprising cysteine in a concentration from about 0.001 to about 1.5% by weight.

33. The skin care treatment of claim 32, further comprising sodium pyroll carboxylate in a concentration of about 0.5% by weight.

34. The skin care treatment of claim 33, further comprising a sodium salt of hyaluronic acid in a concentration of about 0.2% by weight.

35. The skin care treatment of claim 34, further comprising a divalent cation chelator in a concentration which is capable of exfoliating dead skin cells without being irritating to the skin.

36. The skin care treatment of claim 35, wherein the cation chelator is selected from the group consisting of histidine, taurine, and pharmaceutically acceptable derivatives or salts thereof.

37. The skin care treatment of claim 36, wherein the divalent cation chelator is histidine monohydrochloride; monohydrate in a concentration from about 0.1 to 20% by weight.

38. The skin care treatment of claim 37, wherein the concentration of pyridoxine is from about 0.0025% to about 5% by weight, the concentration of pantothenic acid is from about 0.001% to about 2% by weight, and wherein the concentration of N-acetyl-D-glucosamine is from about 0.005% to about 12% by weight.

39. The skin care treatment of claim 38, further comprising a water soluble base.

40. The skin care treatment of claim 39, further comprising a water and lipid emulsion base.

41. A method for human skin care comprising exfoliation and mineral salt chelation by the topical application of a first preparation comprising histidine monohydrochloride: monohydrate in a concentration of at least about 0.1 per cent by weight, followed by the topical application of a second preparation comprising pyridoxine and pantothenic acid wherein the concentration of pyridoxine is from about 0.0025% to about 5% by weight and the concentration of pantothenic acid is from about 0.001% to about 2% by weight.

42. The skin care method of claim 41, wherein the second preparation further comprises N-acetyl-D-glucosamine in a concentration from about 0.005% to about 12% by weight.

43. The skin care method of claim 42, wherein the second preparation further comprises super oxide dismutase in a concentration from about 0.001 to about 4.5% by weight.

44. The skin care method of claim 43, wherein the second preparation further comprises cysteine in a concentration from about 0.001 to about 1.5% by weight.

45. The skin care method of claim 44, wherein the second preparation further comprises tocopherol in a concentration from about 0.001 to about 1.5% by weight.

46. The skin care method of claim 45, wherein the second preparation further comprises sodium pyroll carboxylate in a concentration of about 0.5% by weight.

47. The skin care method of claim 46, wherein the second preparation further comprises the sodium salt of hyaluronic acid in a concentration of about 0.2% by weight.

48. The skin care treatment of claim 47, wherein the first preparation further comprises a water soluble base.

49. The skin care treatment of claim 48, wherein the second preparation further comprises a water and lipid emulsion base.

* * * * *